(12) United States Patent
Zhu

(10) Patent No.: US 7,566,793 B2
(45) Date of Patent: Jul. 28, 2009

(54) PROCESS FOR RESOLVING CITALOPRAM

(75) Inventor: Jie Zhu, Nijmegen (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 12/148,701

(22) Filed: Apr. 22, 2008

(65) Prior Publication Data

US 2008/0281110 A1      Nov. 13, 2008

Related U.S. Application Data

(60) Provisional application No. 60/913,403, filed on Apr. 23, 2007.

(51) Int. Cl.
*C07D 307/87* (2006.01)
(52) U.S. Cl. .................................................. 549/467
(58) Field of Classification Search ................ 549/467
See application file for complete search history.

(56) References Cited

U.S. PATENT DOCUMENTS

| 4,136,193 A | 1/1979 | Bøgesø et al. |
| 4,943,590 A | 7/1990 | Boegesoe et al. |
| RE34,712 E | 8/1994 | Boegesoe et al. |

FOREIGN PATENT DOCUMENTS

| WO | WO 03/006449 | 1/2003 |
| WO | WO 2005/047274 A1 | 5/2005 |

OTHER PUBLICATIONS

C. R. Elati et al., "Substrate Modification Approach to Achieve Efficient Resolution: Didesmethylcitalopram: A Key Intermediate for Escitalopram", Organic Process Research & Development 11 (2), 2007, pp. 289-292.

*Primary Examiner*—Bernard Dentz
(74) *Attorney, Agent, or Firm*—Mark R. Buscher

(57) ABSTRACT

The (S)-citalopram content of a mixture of (R)- and (S)-citalopram can be enriched by using L-tartaric acid as the resolving agent in the presence of formaldehyde.

18 Claims, No Drawings

PROCESS FOR RESOLVING CITALOPRAM

This application claims the benefit of priority under 35 U.S.C. § 119(e) from prior U.S. provisional patent application Ser. No. 60/913,403, filed Apr. 23, 2007; the entire contents of which is incorporated herein by reference.

BACKGROUND OF THE INVENTION

1. Field of the Invention

The present invention relates to a process for resolving enantiomerically impure citalopram into an enriched enantiomeric citalopram compound, and to compounds useful therein.

2. Description of the Prior Art

Citalopram, chemically 1-(3-dimethylaminopropyl)-1-(4-fluorophenyl)-1,3-dihydroisobenzofuran-5-carbonitrile, is a pharmaceutically-active compound that acts as a highly-selective serotonin reuptake inhibitor (SSRI). Citalopram has been disclosed in U.S. Pat. No. 4,136,193. The chemical structure can be represented as follows:

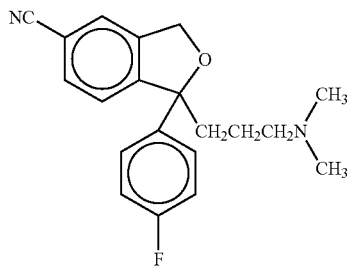

Citalopram has one assymetric carbon (carbon 1 of the dihydroisobenzofuran ring), and thus it may exist in two enantiomeric forms: (S)-citalopram and (R)-citalopram. The pharmacological activity lies predominantly in its (S)-enantiomer, while the (R)-enantiomer is approximately 30-fold less potent.

Racemic citalopram hydrobromide salt has been marketed as an antidepressant for humans under the brand name Celexa® (Forrest Laboratories Inc., St. Louis, Mo. USA). While citalopram was originally marketed as a racemic compound, it has been proposed to administer the substantially pure (S)-enantiomer of citalopram to human patients in order to have fewer side effects. Accordingly, a pharmaceutical formulation comprising the substantially pure (S)-enantiomer of citalopram (generically referred to as escitalopram) has been recently marketed under the brand name Lexapro® (Forrest Laboratories Inc.). The active compound in this medicament is escitalopram oxalate (1:1).

Various production processes yielding substantially enantiomerically pure (S)-citalopram have been reported, including the chromatographic separation of the enantiomers of citalopram (see, e.g., WO 03/006449) and the resolution of citalopram derivatives (see, e.g., Elati et al. (Organic Process Research and Development 11 (2), 289-292, 2007)). U.S. Pat. No. 4,943,590 (reissued as U.S. Pat. No. Re 34,712 and corresponding to EP 0 347 066 B1) reports that previous attempts to crystallize diastereomeric salts of citalopram enantiomers have failed.

WO 03/006449 discloses a chromatographic process for the separation of the enantiomers of citalopram (or an intermediate in the production of citalopram) using a chiral stationary phase. The process is generally economically disadvantageous on an industrial scale due to the high cost of the stationary phase and the low capacity thereof.

Elati et al. reports that "[p]rompted by the ready accessibility of [racemic] citalopram [ ], initially we focused on development of a diastereomeric salt resolution process for [racemic citalopram]" (Organic Process Research and Development 11 (2), at 289-90). Acknowledging the failure reported by U.S. Pat. No. 4,943,590, Elati et al. discloses that "[o]f the many resoluting agents screened, use of (-)-DPTTA [O,O'-di-p-toluoyl-(2R,3R)-tartaric acid], though found to be useful, in our hands proved to be unsatisfactory for an industrial-scale application due to low yields and multiple crystallizations" (Organic Process Research and Development 11 (2), at 290)(citation omitted). As a result, Elati et al. turned to the resolution of a citalopram derivative (as opposed to citalopram itself), which "led to an efficient, scalable, and economic synthesis of [escitalopram]." Also see WO 2005/047274 A1.

In view of the difficulties encountered with resolving citalopram directly using standard crystallization techniques, it would be desirable to have an effective and relatively simple or inexpensive process for resolving racemic citalopram into its enantiomers in high purity, especially a crystallization route suitable for use on an industrial scale.

SUMMARY OF THE INVENTION

The present invention relates to the resolution of citalopram and compounds useful therein. Accordingly a first aspect of the present invention relates to an (S)-enriched citalopram tartrate compound, wherein at least 70% of the citalopram moieties are the (S)-enantiomer of citalopram. Generally, at least 80%, preferably at least 90%, and more preferably at least 95% of the citalopram moieties are the (S)-enantiomer of citalopram.

Another aspect of the invention relates to a process, which comprises treating a diastereomerically impure citalopram tartrate compound with formaldehyde to form (S)-enriched citalopram tartrate compound. Typically, at least 70% of the citalopram moieties of said (S)-enriched citalopram tartrate compound are the (S)-enantiomer of citalopram. The treating step may comprise slurrying and/or suspending diastereomerically impure citalopram tartrate compound in aqueous formaldehyde for a period of time sufficient to form the (S)-enriched citalopram tartrate compound. Alternatively, the treating step may comprise selectively precipitating, in the presence of formaldehyde, the (S)-enriched citalopram tartrate compound from an aqueous medium containing the diastereomerically impure citalopram tartrate compound. The aqueous medium can be formed by combining enantiomerically impure citalopram, L-tartaric acid, and formaldehyde in an aqueous solvent.

A further aspect of the invention relates to a process, which comprises resolving a citalopram tartrate compound in the presence of aqueous formaldehyde in one or more steps to form an (S)-enriched citalopram tartrate compound having at least 90% (S)-citalopram purity; treating said (S)-enriched citalopram tartrate compound with base to form substantially (S)-citalopram; and optionally reacting said substantially (S)-citalopram with oxalic acid to form (S)-citalopram oxalate. The one or more treatment steps used to affect resolution to 90% purity can be the above-mentioned slurrying/suspending technique, selective precipitation, and/or combinations thereof.

DETAILED DESCRIPTION OF THE INVENTION

The present invention is based on the discovery that citalopram may be resolved into its (S)- and (R)-enantiomers (or salts thereof) by the use of inexpensive and readily-available L-tartaric acid and formaldehyde. Although the use of a resolving agent such as L-tartaric acid has generally been unsuccessful when applied to citalopram, leading to the resolution of citalopram derivatives instead, it has been discovered that using the resolving agent L-tartaric acid in combination with formaldehyde surprisingly allows for appreciable resolution of citalopram. The precise mechanism and/or nature of the interaction of the formaldehyde is not clear at this time. One theory, without wishing to be bound thereto, is that the formaldehyde reacts with the tartaric acid, e.g., with the hydroxyl group(s) thereof to form an (hemi)acetal. This reaction could occur before or after the salt forming reaction between tartaric acid and citalopram. Alternatively, the formaldehyde may serve to form a solvate or other co-crystallization former with the citalopram and tartaric acid moieties. Another theory is that the formaldehyde modifies the solvent and/or is the appropriate solvent to provide solubility discrimination between the citalopram tartrate diastereomers.

In any event and regardless of any theory or mechanism, the use of formaldehyde improves the resolution of citalopram by L-tartaric acid as the resolving agent. Thus the process of the invention generally comprises treating a diastereomerically impure citalopram tartrate compound with formaldehyde to form an (S)-enriched citalopram tartrate compound. The term "diastereomerically impure citalopram tartrate compound" refers to the diastereomers produced by reacting enantiomerically impure citalopram (e.g., containing (R)- and (S)-citalopram) with L-tartaric acid. Because this reaction may proceed in the presence of formaldehyde and the precise nature of the formaldehyde interaction is unclear, the citalopram tartrate "compound" designation is intended to also cover the citalopram tartrate salts modified by formaldehyde. The formaldehyde "modification" covers any interaction of the formaldehyde with the citalopram and/or tartaric acid moieties. Such interactions include covalent bonding, e.g., the abovementioned hypothesis of (hemi)acetal formation, ionic bonding, hydrogen bonding, forming a complex, forming a solvate, etc. Some of these interactions, if sufficiently non-transient in nature, would strictly speaking form a new, non-citalopram tartrate compound; e.g. a covalent bond modification resulting in an (hemi)acetal would technically no longer be a tartrate anion as recited. But, for clarity and ease of description, the phrase "citalopram tartrate compound" is used to cover both the expected diastereomeric citalopram tartrate salts and also any modifications thereof caused by formaldehyde. The enantiomerically and diastereomerically "impure" designation means that the ratio of (R) to (S) enantiomeric moieties is in the range of 1:99 to 99:1, and includes a racemic or near racemic mixture having a ratio of 40:60 to 60:40. Furthermore, while the ratio of citalopram and tartrate moieties is normally about 1:1 (analytical values may vary from 1:0.8 to 1:1.2), the citalopram tartrate compound embraces various ratios of citalopram to tartrate ions including about 2:1.

The diastereomerically impure citalopram tartrate compound can be "treated" with the formaldehyde in various ways to form the (S)-enriched citalopram tartrate compound. Generally the treating step involves contacting, or placing in the presence of, formaldehyde with the citalopram tartrate compound, whether solid, dissolved, etc. The treating step can be a separate step from the diastereomeric salt formation or a simultaneous or overlapping step therewith. Two general methods for carrying out the treating step are preferred: a crystallization/precipitation step or a liquid-mediated solid transformation. Each is described hereinafter in further detail.

Crystallization/precipitation techniques for use in the present invention involve selectively precipitating, in the presence of formaldehyde, (S)-citalopram tartrate compound from an aqueous medium containing diastereomerically impure citalopram tartrate compound to form the desired (S)-enriched citalopram tartrate compound. "Selectively precipitating" means that the precipitation favors the precipitation of the (S)-citalopram tartrate compound over the (R)-citalopram tartrate compound from the dissolved form, resulting in a higher percent of (S)-citalopram moiety in the precipitate than was present in the solution. The formaldehyde can be "present" as a free, unassociated molecule in the aqueous medium, as a modification of the citalopram tartrate salt (e.g. covalently bonded to the tartrate ion, complexed with the salt, etc.) or both.

For example, enantiomerically impure citalopram, L-tartaric acid, and formaldehyde can be combined in an aqueous medium in one or more steps to form diastereomerically impure citalopram tartrate compound in an aqueous solution. The aqueous medium/solution is normally stirred to obtain a substantially clear solution. Thereafter precipitation is carried out which selectively precipitates the (S)-citalopram tartrate compound to obtain an (S)-enriched citalopram tartrate compound as a precipitate. The precipitation can be spontaneous or can be assisted by reducing the temperature, adding a seeding crystal, removing solvent, etc. Generally the solution can be formed at ambient temperatures such as 20° C. although higher temperatures can be used. Precipitation is readily carried out at temperatures of 10° C. or less, depending, of course, on the concentration, etc.

The precipitate, which can be crystalline, can be isolated from the stirred solution by conventional separation techniques. For instance, the precipitate can be recovered by filtration or centrifugation, and may be optionally washed and dried.

Conveniently the formaldehyde can be combined as an aqueous formaldehyde. An "aqueous formaldehyde" refers to an aqueous medium comprising formaldehyde dissolved therein. An "aqueous medium" comprises water, and may optionally further contain one or more water miscible organic solvents such as an alcohol, typically methanol or ethanol. For example, the aqueous medium may be water containing up to 30% methanol. Thus the aqueous formaldehyde can be selected from commercially available formaldehyde solutions having a formaldehyde concentration of about 20% or more, generally about 35-37%. Such a solution typically further contains alcohol as a stabilizer, generally approximately 10% methanol. Although the aqueous formaldehyde provides an aqueous medium, additional water can also be incorporated. That is, the use of an aqueous formaldehyde does not preclude the addition or use of additional water or other solvents.

The initial concentration of the citalopram compound dissolved in the aqueous solution is not particularly limited and typically is at least 50 mg/ml and generally in the range of 75 mg/ml to 500 mg/ml. The initial amount of L-tartaric acid added to the aqueous medium is generally at least 1 molar equivalent relative to the citalopram compound, and typically from 1 to 1.2 molar equivalents.

Alternatively, liquid-mediated solid transformation generally involves slurrying and/or suspending the diastereomerically impure citalopram tartrate compound in an aqueous formaldehyde for a period of time sufficient to enrich the (S)-citalopram in the solid citalopram tartrate compound. The slurrying/suspending means that a two phase system is established having solid and liquid phases. Surprisingly treating solid citalopram tartrate compound with aqueous formaldehyde causes an increase in the percent of (S)-citalopram moieties. Without wishing to be bound by theory, it is suspected that small amounts of the solid diastereomer dissolve into the liquid phase and then, spontaneously, selective precipitation of the (S)-diastereomer occurs. Over time, the (R)-citalopram tartrate compound is gradually collected in the liquid phase and the (S)-citalopram tartrate compound is correspondingly collected in the solid phase until equilibrium is reached. In effect, the treatment may be a continuous selective precipitation process. In any event, slurrying or suspending the diasteromerically impure citalopram tartrate compound in aqueous formaldehyde results in an enrichment of the (S)-citalopram moiety in the solid phase. The slurrying/suspending is usually carried out at a temperature of 30° C. or less and typically in the range of −10 to 25° C. for about 1 hour to several days (48-72 hours, etc.), typically 1 to 3 or 4 hours. Generally lower temperatures and longer times improve the yield.

The slurrying/suspending step may be performed a single time, or may be repeated in order to obtain a more enantiomerically-pure (S)-enriched citalopram tartrate compound. For example, slurrying/suspending a single time may obtain an (S)-enriched citalopram tartrate compound in which at least 70% of the citalopram moieties are the (S)-enantiomer of citalopram. Repetition of the slurrying/suspending, each time with new or fresh aqueous formaldehyde (e.g., allowing for a new equilibrium between solid and liquid phases) may obtain an (S)-enriched citalopram tartrate compound in which at least 80%, at least 90%, at least 95%, or at least 99% of the citalopram moieties are the (S)-enantiomer of citalopram. Likewise, the liquid-mediated solid transformation can be used in conjunction with one or more selective precipitations, as previously described, to achieve a desired level of enrichment.

The $^1$H NMR spectrum of an (S)-enriched citalopram tartrate compound typically comprises the characteristic signals of the (S) citalopram, e.g. 7.78 (m, 2H), 7.71 (d, 1H), 7.58 (dd, 2H), 7.16 (t, 2H), 5.21 (ABq, 2H), 2.7 (bs, 2H), 2.47 (s, 6H), 2.23 (m, 2H), 1.44 (bm, 2H) as well as the characteristic signal of the tartaric acid, i.e., 4.04 (s), (all signals expressed in ppm, measured at 400 MHz in DMSO-$d_6$, 60° C.). The (S)-enriched citalopram tartrate compound, typically having higher than 95% (S)-citalopram, is useful for making the (S)-citalopram free base. In a suitable process, the compound is dissolved in water, a molar equivalent of a suitable base is added (typically, an inorganic base, such as sodium hydroxide), and the formed free base of the (S)-citalopram is extracted using an organic solvent immiscible with water (typically EtOAc or dichloromethane). The solid base may be obtained by decreasing the volume of the solution, typically by evaporating the solvent.

The crude (S)-citalopram base product may be purified by recrystallization from a suitable solvent. In general, the starting enantiomeric purity of the product may be enhanced within the isolation process. Typically, the salt product having the original purity of 95% may provide for enantiomerically 99% pure (S)-citalopram base after isolation and one recrystallization. Additional recrystallizations can be carried out if needed, however. The enriched (S)-citalopram base, either in situ (i.e., within the above extract after neutralization of the (S)-citalopram tartrate), or in an isolated form, can be converted to a pharmaceutically acceptable salt, such as the commercially approved oxalic acid salt. The salt can be recrystallized, if desired, one or more times. Ultimately, the enantiomeric purity of the (S)-citalopram, in base or salt form, is preferably sufficiently high, e.g., 99% or greater, so as to be marketable as escitalopram base or pharmaceutically acceptable salt thereof. The escitalopram or its salt can be formulated into pharmaceutical dosage forms such as tablets or capsules as is known in the above-mentioned prior patents. Interestingly, the tartrate salt is also pharmaceutically acceptable and can be used as the active ingredient itself in making a pharmaceutical composition and in treating depression, etc.

The process disclosed above is not limited to starting with racemic citalopram moieties but can be used to improve the enantiomeric purity of any product comprising the (S)-enantiomer of citalopram in a mixture with an (R)-enantiomer (i.e., a non-racemic mixture). Such a product may be, for instance, a product of an unsuccessful or insufficient resolution of the racemate, or an unsuccessful enantioselective synthesis yielding predominantly, but not solely, one of the enantiomers of citalopram. Therefore, the starting material of the above process is not limited to the racemic citalopram, and instead, any mixture of (S) and (R) enantiomers may be used.

The invention will be further described with reference to the following non-limiting examples.

EXAMPLES

Example 1

Resolution of Citalopram to (S)-Citalopram Tartrate Compound 21.9 g (±)-Citalopram, 10.4 g L-(+)-tartaric acid, 60 ml formaldehyde (37%, containing 10-15% methanol), and 40 ml water were stirred at ambient temperature until a clear solution was obtained.

The solution was seeded with 200 mg (+)-Citalopram tartaric acid salt. The mixture was stirred for 5 hours at ambient temperature, and then stirred over night at 4° C. A solid was isolated by filtration.

The solid was suspended in 30 ml formaldehyde (37%, containing 10-15% methanol). The suspension was stirred for 4 hours at ambient temperature. An (S)-citalopram tartrate compound was isolated by filtration. The (S)-citalopram tartrate compound had an enantiomeric purity of 78.3% (S)-citalopram.

The (S)-citalopram tartrate compound, which was not completely dried, was suspended in 25 ml formaldehyde (37%, containing 10-15% methanol). The suspension was stirred for 4 hours at ambient temperature. The (S)-citalopram tartrate compound was isolated by filtration and washed with 2.5 ml water. The (S)-citalopram tartrate compound had an enantiomeric purity of 95% (S)-citalopram.

The (wet) (S)-citalopram tartrate compound was suspended in 18 ml formaldehyde (37%, containing 10-15% methanol). The suspension was stirred at ambient temperature for 4 hours. The (S)-citalopram tartrate compound was isolated by filtration and washed with 2 ml water. The (S)-citalopram tartrate compound had an enantiomeric purity of 97% (S)-citalopram. The (S)-citalopram tartrate compound was dried over night under vacuum at 30° C. The isolated yield was 7.25 g.

Example 2

Formation of (S)-Citalopram Oxalate Using (S)-Citalopram Tartrate Compound 700 mg of the (S)-citalopram tartrate compound was suspended in 30 ml EtOAc and basified (pH to ~10) using 1N aqueous NaOH. The separated EtOAc layer was washed once with brine (10 ml). 700 mg of oxalic acid was added to the EtOAc layer and the resulting mixture was stirred overnight. A (S)-citalopram oxalate was collected by filtration (~400 mg).

Example 3

Resolution of Citalopram to (S)-Citalopram Tartrate Compound

A mixture of 650 mg (±)-Citalopram, 300 mg L-(+)-tartaric acid, and 1 ml 37% formaldehyde was stirred overnight. A solid-like material appeared, and 2 ml of water was added. The solution was stirred for 2 hours.

0.5 ml MeOH was added and the solution was further stirred, resulting in a clear solution. The solution was concentrated in vacuo to almost dry (the pressure was below 20 mbar).

2 ml of 37% formaldehyde was added, and the solution was stirred at room temperature over a weekend.

An (S)-citalopram tartrate compound was filtered off and washed with 2 ml water. About 700 mg (not completely dry) (S)-citalopram tartrate compound was obtained, having an enantiomeric purity of about 74% (S)-citalopram. The filtrate had an enantiomeric purity of about 26% (R)-citalopram.

Example 4

Resolution of Citalopram to (S)-Citalopram Tartrate Compound 9.5 g (±)-Citalopram, 9.0 g L-(+)-tartaric acid, 72 ml formaldehyde (37%), and 36 ml water were stirred at ambient temperature for 2 hours to obtain a clear solution.

The solution was seeded with 200 mg (+)-Citalopram tartaric acid salt. The mixture was stirred over night at 4° C. Then it was stirred at 20° C. for 3 hours, at 4° C. for 3 hours, at 20° C. for 3 hours and further at 4° C. overnight. Solid was collected by filtration.

Obtained solid (wet) was suspended in 20 ml formaldehyde (37%). The suspension was stirred for 2 hours at 15~20° C. An (S)-citalopram tartrate compound was isolated by filtration. The (S)-citalopram tartrate compound had an enantiomeric purity of 88.4% (S)-citalopram.

The (S)-citalopram tartrate compound, which was not completely dried, was suspended in 20 ml formaldehyde (37%). The suspension was stirred for 2 hours at 15~20° C. The (S)-citalopram tartrate compound was isolated by filtration. The (S)-citalopram tartrate compound had an enantiomeric purity of 92.4% (S)-citalopram.

The (wet) (S)-citalopram tartrate compound was suspended in 15 ml formaldehyde (37%). The suspension was stirred at 15~20° C. for 2 hours. The (S)-citalopram tartrate compound was isolated by filtration. The (S)-citalopram tartrate compound had an enantiomeric purity of 95.8% (S)-citalopram.

The (wet) (S)-citalopram tartrate compound was suspended in 10 ml formaldehyde (37%). The suspension was stirred at 15~20° C. for 2 hours. The (S)-citalopram tartrate compound was isolated by filtration. The (S)-citalopram tartrate compound was dried over night under vacuum at 40° C. The (S)-citalopram tartrate compound had an enantiomeric purity of 98.6% (S)-citalopram.

Example 5

Formation of (S)-Citalopram Oxalate Using (S)-Citalopram Tartrate Compound

A mixture containing 10 kg of (S)-citalopram tartrate compound in 50 L of toluene and 30 L of water was stirred and followed by addition of 2 L of concentrated ammonia solution to adjust the aqueous pH to 9~10. The pH was re-adjusted after stirring for ~20 mins. Layers were separated, and the aqueous phase was extracted with 25 L of toluene. Combined toluene layer was washed with 20 L of saturated brine and 20 L of water, respectively. The toluene layer was dried over anhydrous magnesium sulfate, and concentrated in vacuo at 50~60° C. to obtain a yellow oily mass.

The oily mass was dissolved in 30 L of anhydrous ethanol and stirred at ambient temperature. Anhydrous ethanol solution of oxalic acid (2 kg of oxalic acid dissolved in 5 L of ethanol) was added dropwise into above solution. After the addition, it was further stirred for ~30 mins. Then the batch was cooled to ~5° C., and further stirred for ~10 hours. Centrifuged, the cake was washed with 2 L of anhydrous ethanol. The (S)-citalopram oxalate was further dried at 50° C. in vacuo for ~8 hours. 8.5~9.5 kg (S)-citalopram oxalate was obtained.

Each of the patents and application mentioned above are incorporated herein by reference. The invention having been described it will be obvious that the same may be varied in many ways and all such modifications are contemplated as being within the scope of the invention as defined by the following claims.

I claim:

1. An (S)-enriched citalopram tartrate compound, wherein at least 70% of the citalopram moieties are the (S)-enantiomer of citalopram.

2. The (S)-enriched citalopram tartrate compound according to claim 1, wherein at least 80% of the citalopram moieties are the (S)-enantiomer of citalopram.

3. The (S)-enriched citalopram tartrate compound according to claim 2, wherein at least 90% of the citalopram moieties are the (S)-enantiomer of citalopram.

4. The (S)-enriched citalopram tartrate compound according to claim 3, wherein at least 95% of the citalopram moieties are the (S)-enantiomer of citalopram.

5. The (S)-enriched citalopram tartrate compound according to claim 4, wherein said (S)-enriched citalopram tartrate compound is in a solid physical form.

6. A process, which comprises treating a diastereomerically impure citalopram tartrate compound with formaldehyde to form an (S)-enriched citalopram tartrate compound.

7. The process according to claim 6, where said treating step comprises slurrying and/or suspending said diastereomerically impure citalopram tartrate compound in aqueous formaldehyde for a period of time sufficient to form said (S)-enriched citalopram tartrate compound.

8. The process according to claim 7, which further comprises slurrying and/or suspending said (S)-enriched citalopram tartrate compound in aqueous formaldehyde for a sufficient time to form a further enriched (S)-enriched citalopram tartrate compound.

9. The process according to claim 8, wherein at least 95% of the citalopram moieties of said further enriched (S)-enriched citalopram tartrate compound are the (S)-enantiomer of citalopram.

10. The process according to claims 9, which further comprises converting said (S)-enriched citalopram tartrate compound to (S)-enriched citalopram or a pharmaceutically acceptable salt thereof.

11. The process according to claim 6, wherein said treating step comprises selectively precipitating, in the presence of formaldehyde, (S)-enriched citalopram tartrate compound from an aqueous medium containing said diastereomerically impure citalopram tartrate compound to form said (S)-enriched citalopram tartrate compound.

12. The process according to claim 11, which further comprises combining enantiomerically impure citalopram, L-tartaric acid, and formaldehyde in an aqueous solvent to form said diastereomerically impure citalopram tartrate compound in said aqueous medium.

13. The process according to claim 12, wherein said diastereomerically impure citalopram tartrate compound contains (S) and (R) enantiomers of citalopram in a ratio of about 40:60 to 60:40.

14. The process according to claims 13 wherein at least 70% of the citalopram moieties of said (S)-enriched citalopram tartrate compound are the (S)-enantiomer of citalopram.

15. The process according to claims 14 wherein at least 80% of the citalopram moieties of said (S)-enriched citalopram tartrate compound are the (S)-enantiomer of citalopram.

16. The process according to claim 11, which further comprises converting said (S)-enriched citalopram tartrate compound to (S)-enriched citalopram or a pharmaceutically acceptable salt thereof.

17. A process, which comprises:
resolving a citalopram tartrate compound in the presence of aqueous formaldehyde in one or more steps to form an (S)-enriched citalopram tartrate compound having at least 90% (S)-citalopram purity;
treating said (S)-enriched citalopram tartrate compound with base to form substantially (S)-citalopram; and optionally
reacting said substantially (S)-citalopram with oxalic acid to form (S)-citalopram oxalate.

18. In a process for resolving enantiomerically impure citalopram via diastereomeric salt crystallization, the improvement for which comprises using L-tartaric acid as the resolving agent in the presence of formaldehyde.

* * * * *